(12) United States Patent
Ahong et al.

(10) Patent No.: US 11,756,407 B2
(45) Date of Patent: Sep. 12, 2023

(54) HYGIENE MONITORING SYSTEMS AND METHODS

(71) Applicant: Essity Hygiene and Health Aktiebolag, Gothenburg (SE)

(72) Inventors: Timothy Ahong, Mississauga (CA); Shyam Mali, Etobicoke (CA); Danny Porthiyas, Toronto (CA); Joel Ironstone, Toronto (CA); Jacob Edding, Mississauga (CA); Martin Rozee, Mississauga (CA)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/757,471

(22) PCT Filed: Nov. 17, 2017

(86) PCT No.: PCT/EP2017/079676
§ 371 (c)(1),
(2) Date: Apr. 20, 2020

(87) PCT Pub. No.: WO2019/096414
PCT Pub. Date: May 23, 2019

(65) Prior Publication Data
US 2021/0192925 A1 Jun. 24, 2021

(51) Int. Cl.
*G08B 21/24* (2006.01)
*G16H 40/67* (2018.01)
(Continued)

(52) U.S. Cl.
CPC .......... *G08B 21/245* (2013.01); *G16H 40/20* (2018.01); *G16H 40/67* (2018.01); *H04W 4/80* (2018.02)

(58) Field of Classification Search
CPC ...... G08B 21/245; G16H 40/67; G16H 40/20; H04W 4/80
See application file for complete search history.

(56) References Cited

U.S. PATENT DOCUMENTS 5,686,902 A * 11/1997 Reis .................. G01S 13/74
340/8.1
8,196,809 B2 6/2012 Thorstensson
(Continued)

FOREIGN PATENT DOCUMENTS

| CN | 101040286 A | 9/2007 |
| CN | 101287405 A | 10/2008 |

(Continued)

OTHER PUBLICATIONS

National Intellectual Property Administration (CNIPA) of the People's Republic of China, Notification of the First Office Action, Application No. 201780096735.0, dated Sep. 21, 2020 (15 pages).
(Continued)

*Primary Examiner* — James J Yang
(74) *Attorney, Agent, or Firm* — CANTOR COLBURN LLP

(57) ABSTRACT

A method of associating a hygiene monitoring device to a station device, the hygiene monitoring device being configured to monitor a hygienic state of a user, the method comprising: the hygiene monitoring device obtaining, when in use, an station identifier from the station device; and the hygiene monitoring device storing the station identifier. A hygiene monitoring device for this method and a system comprising the hygiene monitoring device and the station device.

22 Claims, 8 Drawing Sheets

(51) Int. Cl.
    *G16H 40/20*    (2018.01)
    *H04W 4/80*    (2018.01)

(56) References Cited

U.S. PATENT DOCUMENTS

| | | | |
|---|---|---|---|
| 8,308,640 | B2 | 11/2012 | Baldus et al. |
| 2007/0270774 | A1* | 11/2007 | Bergman ............... G16H 40/60 604/361 |
| 2011/0254682 | A1 | 10/2011 | Sigrist Christensen |
| 2013/0012896 | A1 | 1/2013 | Suzuki et al. |
| 2014/0320289 | A1* | 10/2014 | Raichman ............ G08B 21/245 340/573.1 |
| 2016/0134497 | A1 | 5/2016 | Oloffson Ranta et al. |
| 2017/0309155 | A1 | 10/2017 | Tallent et al. |

FOREIGN PATENT DOCUMENTS

| | | | |
|---|---|---|---|
| CN | 101730856 | A | 6/2010 |
| CN | 103547926 | A | 1/2014 |
| JP | 2008537502 | A | 9/2008 |
| JP | 2011147505 | A | 8/2011 |
| JP | 2012502343 | A | 1/2012 |
| JP | 2016049401 | A | 4/2016 |
| JP | 2016524131 | A | 8/2016 |
| JP | 2016170070 | A | 9/2016 |
| JP | 2017000707 | A | 1/2017 |
| JP | 2017150889 | A | 8/2017 |
| WO | 2006105269 | A1 | 10/2006 |
| WO | 2013151933 | A1 | 10/2013 |
| WO | 2016090492 | A1 | 6/2016 |
| WO | 2016190008 | A1 | 12/2016 |

OTHER PUBLICATIONS

European Patent Office, International Search Report and Written Opinion of the International Searching Authority, International Application No. PCT/EP2017/079676, dated Aug. 9, 2018 (12 pages).

Japanese Patent Office, Notice of Reasons for Rejection, Application No. 2020-527056, dated Jul. 5, 2021 (8 pages).

Journal of Practical Electrocardiology, Remote ECG Monitoring Technology, vol. 25, No. 2, Apr. 2016 (4 pages).

Rim Negra et al. / Procedia Computer Science, Wireless Body Area Networks: Applications and technologies, 83 (2016) 1274-1281 (8 pages).

China National Intellectual Property Administration, Notice of Granting Patent Right for Invention, Application No. 201780096735.0, dated Apr. 8, 2021 (8 pages).

Australian Government, IP Australia, Examination report No. 1 for standard patent application, Application No. 2017439488, dated Mar. 19, 2021 (5 pages).

Japanese Patent Office, Notice of Reasons for Rejection, Application No. 2020-526934, dated Jul. 5, 2021 (8 pages).

Examination Report issued in Australian Application No. 20170439488; Application Filing Date Nov. 17, 2017; dated Jan. 27, 2022 (6 pages).

Office Action issued in Japanese Application No. 20200526934; Application Filing Date Nov. 17, 2017; dated Feb. 14, 2022 (8 pages).

Priyantha et al., "The cricket location-support system" Proceedings of the 6th annual international conference on Mobile computing and networking; (Aug. 2000) pp. 32-43.

Decision to Grant issued in Japanese Application No. 20200526934; Application Filing Date Nov. 17, 2017; dated Sep. 5, 2022 (5 pages).

Office Action issued in Chinese Application No. 201780096740.1; Application Filing Date Nov. 17, 2017; dated Mar. 15, 2023 (28 pages).

Search Report and Written Opinion issued in Brazil Application No. 112020008334-8; Application Filing Date Nov. 17, 2017; dated May 25, 2023 (4 pages).

* cited by examiner

HYGIENE MONITORING SYSTEMS AND METHODS

CROSS-REFERENCE TO RELATED APPLICATION

The present application is a national stage entry under 35 U.S.C. § 371 of, and claims priority to, International Application No. PCT/EP2017/079676, filed Nov. 17, 2017, the disclosure of which is hereby incorporated herein by reference in its entirety.

FIELD OF THE INVENTION

The present disclosure relates to hygiene monitoring systems and methods, and, in particular, systems and methods for associating a hygiene monitoring device to a station device.

BACKGROUND OF THE INVENTION

A hygiene monitoring device may be used to monitor a hygienic state of a user, or a hygienic state of a hygiene article worn by the user. For example, a hygiene monitoring device may monitor a wetness level, a temperature and/or a concentration of a particular substance associated with the user. In certain situations, the hygiene monitoring device may be attached to a hygiene article which is worn by the user, such a disposable absorbent hygiene article, for example a diaper, incontinence protection or sanitary napkin, or it may alternatively be attached to a piece of clothing, for example, to monitor the presence of gas indicative of faecal matter, allowing the device to be used for faecal detection. Typically, the hygiene monitoring device transmits information relating to the monitored hygienic state of the user, such as a soiling event.

In residences, such as care homes, hospitals and the like, where residents are under the care of caregivers, several hygiene monitoring devices may be interchangeably used with several different residents (for example, the hygiene monitoring devices may be used with different residents during different periods, such as different days). In certain devices, the hygiene monitoring device may alert a caregiver when it detects a change in the hygienic state of a user, such as a soiling event. In such cases, the hygiene monitoring device may communicate the information relating to the monitored hygienic state of the resident to a common, centralised monitoring system which is configured to alert a caregiver of a change in the hygienic state. The centralised monitoring system alerts the caregiver as to which resident needs attention so that the caregiver may attend to this resident. Hereinafter the disclosure is exemplified with regard to care homes, but the disclosure is equivalently applicable to hospitals, nurseries, and other institutional facilities.

Accordingly, during every period, the information being received by the centralised monitoring system from each of the hygiene monitoring devices must be associated with one particular resident such that the centralised monitoring system may notify the caregiver which resident needs tending to. To this end, typically, each hygiene monitoring device has a unique serial number which is transmitted to the centralised monitoring system along with the information relating to the hygienic state.

However, in such systems, the caregiver must manually log on the centralised monitoring system which serial number (corresponding to a hygiene monitoring device) is associated with which resident.

As care homes tend to be busy places and hygiene monitoring devices are often switched between residents, it has been found that caregivers either forget or inaccurately assign (or re-assign) the hygiene monitoring device with the correct residents. This causes the possibility for the hygiene information to be associated with the wrong resident, leading to a poor standard of care. For example, the wrong resident's hygiene article may be replaced.

In addition, information on the state of a hygiene article is confidential due to its medical nature. There is therefore a need to prevent or hinder unauthorised access to this information, and/or to prevent unauthorised parties from associating this information to a specific resident. Depending on the jurisdiction, specific laws or rules defining the level of care may have to be followed by systems in care residences.

Accordingly, there is a need for improved hygiene monitoring which allows for information from a hygiene monitoring device to be conveniently and reliably associated to the correct resident, while preserving confidentiality of the information.

SUMMARY OF THE INVENTION

According to an aspect of the present disclosure, there is provided a method of associating a hygiene monitoring device to a station device, the hygiene monitoring device being configured to monitor a hygienic state of a user, the method comprising the hygiene monitoring device obtaining, when in use, a station identifier from the station device, and the hygiene monitoring device storing the station identifier.

With the above method, the station device may be placed within the care home (or other residence), permanently or semi-permanently, so that it is associated with a spatial location unique for a resident, such as a room or a bed, for example, by placing it next to the bed, which is in turn associated with a resident normally occupying the bed. The station device may be installed permanently or semi-permanently by fixing it to a structural element of the care home, such as a wall, ceiling or floor.

The hygiene monitoring device may be wearable by a user and configured to monitor a hygienic state of a user wearing it, or it may be attachable to a piece of clothing or hygiene article to be worn by the user.

Accordingly, the caregiver may conveniently associate the hygiene monitoring device with the station device during its use. As the station device (and, accordingly the corresponding station identifier) is associated with the particular spatial location (e.g., the bed), which is in turn associated with a particular resident, upon obtaining the station identifier, the hygiene monitoring device stores the station identifier which is associated with the station device, which, in turn is associated with the spatial location, such as the bed, which, in turn is associated with a particular resident. It has been observed that residents change beds much less often than monitoring devices need to be reassigned between residents.

If the hygiene monitoring device is to be used with another resident, the caregiver easily associates the hygiene monitoring device with the station device associated with the other resident's bed (such as a station next to their bed), thereby conveniently and reliably obtaining another station identifier by the hygiene monitoring device.

With the above method, the necessity for manual input to associate the hygiene monitoring device and a resident (or another resident) is avoided. Therefore, any human-error factor is severely reduced. By associating the hygiene monitoring device, and, consequently, the hygiene article, with a station device, rather than a resident directly, information on the state of the hygiene article obtained by unauthorised parties cannot be easily associated with any specific resident.

Hence, with such a method, it is possible to provide an improved hygiene monitoring method which allows for information from a hygiene monitoring device to be conveniently and reliably associated to the correct resident, while preserving confidentiality of the information.

In one implementation, the hygiene monitoring device obtains the station identifier when placed within a defined spatial region in the proximity of the station device.

Accordingly, because the hygiene monitoring device is placed in the proximity of the station device to obtain the identifier, the risk of inadvertently associating an incorrect hygiene monitoring device with a station device is reduced, and therefore improves the accuracy of association of the devices.

In this case, because the hygiene monitoring device is placed within a defined spatial region in the proximity of the station device, obtaining the station identifier by the hygiene monitoring device provides an indication of a spatial relationship between the hygiene monitoring device and the station device, which can be used to locate the hygiene monitoring device.

In one implementation, the hygiene monitoring device is removably attachable to a hygiene article and configured to monitor a hygienic state of the hygiene article.

Accordingly, when the hygiene monitoring device is attached to a hygiene article worn by a user, the hygienic state of the user may be inferred from the hygienic state of the hygiene article.

Additionally, the hygiene article may be removed from the hygiene article and attached to a different hygiene article, for example, when the hygiene monitoring device is used with disposable hygiene articles.

In one implementation, the hygiene monitoring device transmits the stored station identifier. In one implementation, information indicative of a hygienic state is transmitted together with the stored station identifier.

The transmitted information may be indicative of the hygienic state of the user, or, the information transmitted information may be indicative of the hygienic state of the hygiene article.

Accordingly, an external device receiving the stored station identifier and optionally the information indicative of the hygienic state can associate the hygienic state of the hygiene article with the station device corresponding to the station identifier.

In one implementation, the hygiene monitoring device stores a device identifier. The hygiene monitoring device transmits the stored station identifier together with the device identifier. In one implementation, the hygiene monitoring device transmits information indicative of the hygienic state together with the device identifier.

Accordingly, an external device receiving the device identifier and the station identifier may associate the hygiene monitoring device and the station device.

Additionally, an external device receiving information indicative of the hygienic state together with the device identifier can associate the hygienic state of the hygiene article with the hygiene monitoring device corresponding to the device identifier, and thus with the station device corresponding to the station identifier associated with the device identifier.

In one implementation, the station device receives information transmitted by the hygiene monitoring device.

The information received may be one or more of the station identifiers, the device identifier and information indicative of the hygienic state of the hygiene article. Additionally or alternatively, the information may indicate a state of the hygiene monitoring device, such as a monitoring state corresponding to the hygiene monitoring device monitoring the hygienic state of the hygiene article, a charging state corresponding to the hygiene monitoring device being charged, or an abnormal state corresponding to the hygiene monitoring device being unable to monitor the hygienic state at a desired accuracy. Additionally, or alternatively, the information may indicate that a station identifier was successfully obtained and stored.

In one implementation, the station device verifies whether the station identifier is correctly obtained and/or stored by the hygiene monitoring device.

In one implementation, the station device transmits the station identifier wirelessly.

In one implementation, the station identifier is transmitted via a standards-based short range communication protocol, such as near-field communication (NFC), infra-red communication (IR, for example IRdA), a personal area network (PAN such as Bluetooth™), RFID, and the like, or may be transmitted via an sonic signal, such as an ultrasound signal (i.e., an sonic signal with a frequency outside the range detectible by the human ear, for example a frequency above 20 kHz).

In one implementation, the station device provides the station identifier continuously or provides the station identifier selectively, based on a predetermined condition.

Accordingly, the hygiene monitoring device can obtain the station identifier from the station device without requiring an interaction between the hygiene monitoring device and the station device.

The predetermined condition may be any condition enabling the station device to determine when to provide the station identifier. The station device may, for example, provide the station identifier when a hygiene monitoring device is placed on or in the station device when the hygiene monitoring device is removed from the station device, when a user interaction is performed with the station device, such as touching a touch element or pressing a button, or the station device may provide the station identifier at predetermined intervals.

In one implementation, the station device broadcasts the station identifier to provide it (continuously or selectively).

In one implementation, the hygiene monitoring device transmits the stored station identifier, and a receiving entity receives the station identifier from the hygiene monitoring device. The receiving entity determines a spatial location corresponding to the station device, based on the received station identifier.

The determination of a spatial location corresponding to the station device, allows in turn the determination of a spatial location corresponding to the hygiene monitoring device having transmitted the station identifier.

In one implementation, the hygiene monitoring device transmits the device identifier together with the stored station identifier. A receiving entity receives the station identifier and the device identifier from the hygiene monitoring device, and associatively stores the device identifier and the station identifier. The receiving entity determines a spatial location corresponding to the station device, based on the received station identifier.

The determination of a spatial location corresponding to the station device, allows in turn the determination of a spatial location corresponding to the hygiene monitoring device having transmitted the station identifier.

In one implementation, the spatial location is determined based on a pre-stored correspondence between the station identifier and the spatial location.

In one implementation, the receiving entity receives information indicative of the hygienic state. In one implementation, the receiving entity notifies of a hygienic event and a corresponding spatial location.

In one implementation, the receiving entity notifies of a hygienic event and a corresponding spatial location by triggering a notification to one or more notification devices the notification comprising at least information on a determined spatial location. The notification device may be adapted to display notifications corresponding to one of a predetermined set of spatial location.

In one implementation, the notification device may be associated with a set of possible spatial locations and may be adapted to display only notifications notifying of a spatial location comprised in the set of possible spatial locations.

For example, the notification device may be adapted to selectively display notifications when the notification comprises information on a spatial location included in a predetermined set of spatial locations associated with the notification device. Each notification device may be associated with a different set of spatial locations, or alternatively, a plurality of notification devices may be associated with a same specific spatial location, for example, by including the specific spatial location into each set of spatial locations associated with each notification devices.

Accordingly, the possible spatial locations in a care home may be divided into subsets of spatial locations and notification devices may be associated with one or more of the subsets of spatial locations.

In other implementations, the receiving entity may be configured to notify of a hygienic event and/or a spatial location directly, without triggering a notification to a notification device.

According to a second aspect of the present disclosure, there is provided a hygiene monitoring device configured to monitor a hygienic state of a user. The hygiene monitoring device comprises an identification module configured to obtain, when in use, a station identifier from a station device, and to store the station identifier.

The above hygiene monitoring device can therefore be associated with a station device without requiring manual association. The station device can be associated in turn with a bed within a care home. The hygienic state of the hygiene article monitored by the hygiene monitoring device can be associated with the station identifier, and therefore the corresponding station device.

Because the hygienic state is not associated directly with a resident, but is, instead, associated with a station device, or with a bed, the device reduces the possibility that information on the hygienic state is used to identify the resident wearing or carrying the hygiene article.

Hence, with such a device, it is possible to provide an improved hygiene monitoring device which allows for information from the hygiene monitoring device to be conveniently and reliably associated to the correct resident, while preserving confidentiality of the information.

In an embodiment, the identification module is configured to obtain the station identifier when the hygiene monitoring device is placed within a defined spatial region in the proximity of the station device.

In an embodiment, the hygiene monitoring device is removably attachable to a hygiene article and the hygiene monitoring device is configured to monitor a hygienic state of the hygiene article.

In an embodiment, the hygiene monitoring device comprises a transmission module configured to transmit the stored station identifier.

In an embodiment, the identification module is configured to store a device identifier, and the transmission module configured to transmit the stored station identifier together with the device identifier.

In an embodiment, the hygiene monitoring device is configured to transmit information indicating a hygienic state. In an embodiment, this may be information indicative of the hygienic state of the user, or information indicative of the hygienic state of the hygiene article.

According to a third aspect of the present disclosure, there is provided a hygiene monitoring system. The hygiene monitoring system comprises a hygiene monitoring device configured to monitor a hygienic state of a user, such as a hygiene monitoring device removably attachable to a hygiene article and configured to monitor a hygienic state of the hygiene article. The hygiene monitoring system comprises a station device configured to provide a station identifier to the hygiene monitoring device.

With such a system, it is possible to provide an improved hygiene monitoring device which allows for information from the hygiene monitoring device to be conveniently and reliably associated to the correct resident, while preserving confidentiality of the information. In an embodiment, the hygiene monitoring system comprises a receiving entity configured to obtain any two of a station identifier, a device identifier and information indicating a hygienic state of a hygiene article. In certain embodiments, the receiving entity is configured to determine a spatial location corresponding to the station identifier.

In certain embodiments, the receiving entity is configured to determine a station device corresponding to the received station identifier, and to determine a spatial location corresponding to the station device.

The receiving entity may determine the spatial location based on a received station identifier or based on a received device identifier and a pre-stored association between the received device identifier and a station identifier corresponding to the station device.

In an embodiment, the receiving entity is configured to receive information indicative of the hygienic state of the hygiene article. In an embodiment, the receiving entity is configured to notify of a hygienic event and a corresponding spatial location.

Accordingly, the receiving entity is capable of alerting a caregiver assigned to the spatial location corresponding to the station device, of a hygienic event having occurred in connection with the hygiene monitoring device (and, therefore, the hygiene article and the resident wearing or carrying the hygiene article), and of providing a spatial location corresponding to the station device, from which, in turn, a specific bed in the care home can be determined.

In one embodiment the system may comprise at least one notification device each adapted to display a notification corresponding to a hygienic event and a corresponding spatial location. In some embodiments, the at least one notification device may be configured to display notifications corresponding to one of a predetermined set of spatial locations.

In an embodiment, the station device is configured to store the hygiene monitoring device and/or to charge the hygiene monitoring device; and wherein the station device is configured to provide the station identifier to the hygiene monitoring device when the hygiene monitoring device is stored and/or being charged by the station device.

Accordingly, the caregiver can place the hygiene monitoring device on or in the station device before being removably attached to a hygiene article, to associate the hygiene monitoring device with the station device (and, therefore, the bed and/or resident normally occupying the bed) while storing and/or charging the hygiene monitoring device.

The hygiene monitoring device may also be placed on or in a second station device after having been removably attached to a hygiene article and associated with a first station device. The thus placed hygiene monitoring device can therefore be assigned to the second station device and removably attached to a second hygiene article different from the first article.

Hence, the above described methods, devices and systems, it is possible to provide an improved hygiene monitoring which allows for information from a hygiene monitoring device to be conveniently and reliably associated to the correct resident, while preserving confidentiality of the information.

In the embodiments and implementations described herein, the hygiene monitoring device may be wearable by a user and configured to monitor a hygienic state of a user wearing it, or it may be attachable to a piece of clothing or hygiene article to be worn by the user.

In the embodiments and implementations described herein, the hygiene monitoring device needs not be attached to a hygiene article to obtain and store a station identifier, or more generally to be considered "in use". Generally, the hygiene monitoring device can be considered in use whenever it is handled by a caregiver or a user.

In the embodiments and implementations described herein, the station identifier may be any information that allows for a station device to be differentiated from other station devices, or for a spatial location, such as bed to be differentiated from other spatial locations, beds, and which corresponds to the station device (or to the bed).

For example, 'station identifier' also refers to any manipulated (e.g., encrypted, hashed, signed or otherwise processed) version of the stored identifier. The station identifier may be obtained, stored and/or transmitted in their original forms or in a manipulated version.

Accordingly, the transmission of information from the station device and/or from the hygiene monitoring device may be encrypted for further security.

In some embodiments and implementations described herein, the station identifier may uniquely identify the station. The station identifier may be a code such as an alphanumeric code, which uniquely identifies the station device, and can correspond to a global unique station identifier (GUID) or a universally unique station identifier (UUID) such as an IMEI number, IP address or MAC address. In this case, the hygiene monitoring device is associated with the station device by storing the corresponding station identifier.

In some embodiments and implementations described herein, the station identifier may be indicative of the location of the bed in the care home, for example, by indicating the room, floor, bed number, or other information indicating the bed associated with the station device.

In some embodiments and implementations described herein, the station identifier is stored for subsequent access by the hygiene monitoring device or a device external to the hygiene monitoring device. For example, in some cases, the hygiene monitoring device may subsequently transmit the stored station identifier to an external device. In other cases, the external device (e.g., the station device) may retrieve the station identifier stored in the hygiene monitoring device, together with other information, such as information indicating the hygienic state of a hygiene article, information on a state of the hygiene monitoring device, and the like. This transmission or retrieval of the stored station identifier may provide an indication to the external device of the association between the hygiene monitoring device and a station device. In turn, this association may indicate a spatial relationship between the station device and the hygiene monitoring device having obtained it.

In other embodiments and implementations, access to the stored station identifier may be restricted and the station identifier may be used in encryption of transmitted information.

In embodiments and implementations described herein, the hygiene monitoring device may replaceably store the station identifier. In some embodiments or implementations, the hygiene monitoring device may have stored a first station identifier, and a second station identifier different from the first station identifier may be subsequently obtained and stored to replace the first station identifier. In some embodiments or implementations, the hygiene monitoring device may be disassociated from the station device, and the stored station identifier may be replaced by a default piece of information or a random piece of information, to indicate that the hygiene monitoring device is not (or no longer) associated with a station device. Accordingly, the risk of a caregiver being wrongly alerted of a hygienic event is diminished.

In some embodiments or implementations described herein, an area substantially surrounding the station device may be defined as the spatial region, and the hygiene monitoring device may obtain the station identifier by being in proximity of the station device, that is, within a predetermined distance of the station device. Then, associating the hygiene monitoring device and the station device may indicate a spatial relationship between the two devices, for example, by indicating that the hygiene monitoring device is or was located in the proximity of the station device.

In some embodiments or implementations where the station device broadcasts the station identifier, the spatial region may, for example, cover the entire region from which the broadcast station identifier may be obtained and interpreted by a hygiene monitoring device.

In other embodiments or implementations described herein, the spatial region may be limited directionally. The hygiene monitoring device may obtain the station identifier by being in proximity of the station device, that is, the hygiene monitoring device being within a predetermined distance of the station device and being at or about a relative direction relative to the station device. In such a configuration, NFC or IR communication may be particularly advantageous, since such communication is only generally possible when the monitoring device and station device are in predetermined locations, or within predetermined ranges.

In some embodiments or implementations described herein, the hygiene monitoring device may use wired or wireless transmission to recurrently transmit information such as the station identifier, the device identifier and/or the information indicative of a hygienic state of the hygiene article. In other embodiments, the hygiene monitoring device may store the information to be transmitted and transmit the stored information at a single occasion.

In some embodiments and implementations described herein as transmitting an identifier together with another identifier or with information indicative of a hygienic state, the pieces of information (including the identifiers) being transmitted together are transmitted simultaneously or contemporaneously, for example, by forming part of the same message, either as part of a payload or as forming part of an overhead or header. In other embodiments and implementations, the pieces of information are transmitted at a predetermined interval from one another, for example, by transmitting an identifier (a station identifier or a device identifier), an transmitting the information indicative of a hygienic state 1 millisecond afterwards.

In some embodiments and implementations described herein, the device identifier may be any information which allows for a hygiene monitoring device to be identified and differentiated from other hygiene monitoring devices. Similarly, to the station identifier, the device identifier may uniquely identify the hygiene monitoring device, and may be a globally unique identifier, a universally unique identifier, an alphanumeric code identifying the hygiene monitoring device or the like.

Similarly, to the station identifier, the term 'device identifier' also refers to any manipulated (e.g., encrypted, hashed, signed or otherwise processed) version of the stored identifier. The device identifier may therefore be stored and/or transmitted in their original forms or in a manipulated version.

Accordingly, the transmission of information from the station device and/or from the hygiene monitoring device may be encrypted for further security.

In some embodiments and implementations described herein, the device identifier is transmitted together with a station identifier. Subsequently, the information indicative of the hygienic state is transmitted with the device identifier only.

Accordingly, it is possible to associatively store the device identifier to a station identifier, and therefore, to a station device (or to a bed), and, to determine a corresponding station device for any subsequent transmission of information indicative of a hygienic state, based on the previously stored association between device identifier and station identifier. Therefore, even if a subsequent transmission which includes only the device identifier and information indicative of a hygienic state is accessed by unauthorised parties, the information cannot lead to the identification of a specific resident of the care home, and the confidentiality of information is maintained.

In the embodiments and implementations referring to a receiving entity, this entity may be implemented as a single device or a plurality of devices that are communicatively coupled to one another. Preferably, the receiving entity comprises a gateway configured to receive information from the hygiene monitoring device and to forward the received information to a server centrally storing the received information, for example comprising one or more database of associations between station identifiers and spatial locations corresponding to station devices, between device identifiers and station identifiers, a database of the hygienic state of hygiene article, a database of the state of hygiene monitoring devices and the like.

In embodiments and implementations described herein, the receiving entity may have associatively stored a received device identifier and a station identifier. The receiving entity may subsequently receive the device identifier together with the new station identifier and update its stored records to associatively store the device identifier with the new station identifier.

In one embodiment, the hygiene monitoring device comprises a battery. The station is configured to charge the battery when the hygiene monitoring device is received in the station.

In one embodiment, the station is a charging station for the hygiene monitoring device.

In one embodiment, hygiene monitoring device is configured to monitor wetness level, a temperature, a presence of an analyte and/or a concentration of a particular substance (liquid or gas) associated with the user.

In one embodiment, the hygiene monitoring device comprises a biosensor.

In one embodiment, the hygiene monitoring device is removably attachable to a wearable hygiene article. In one embodiment, the hygiene monitoring device comprises Velcro.

In one embodiment, the wearable hygiene article is a disposable absorbent article, such as a diaper or incontinence shield.

In one embodiment, the hygiene monitoring device is configured to store the identifier. In one embodiment, the hygiene monitoring device is configured to transmit the identifier together with any sensed data.

In one embodiment, the hygiene monitoring device is re-useable.

In one embodiment, the hygiene monitoring device comprises a cell.

In one embodiment, the hygiene monitoring device is rechargeable.

In one embodiment, the hygiene monitoring device comprises a replaceable cell.

In one embodiment, the hygiene monitoring device is disposable.

BRIEF DESCRIPTION OF THE DRAWINGS

In the following, aspects of the present disclosure will be described by reference to the following drawings, by way of example only, in which.

DETAILED DESCRIPTION OF THE INVENTION

Figure 1:
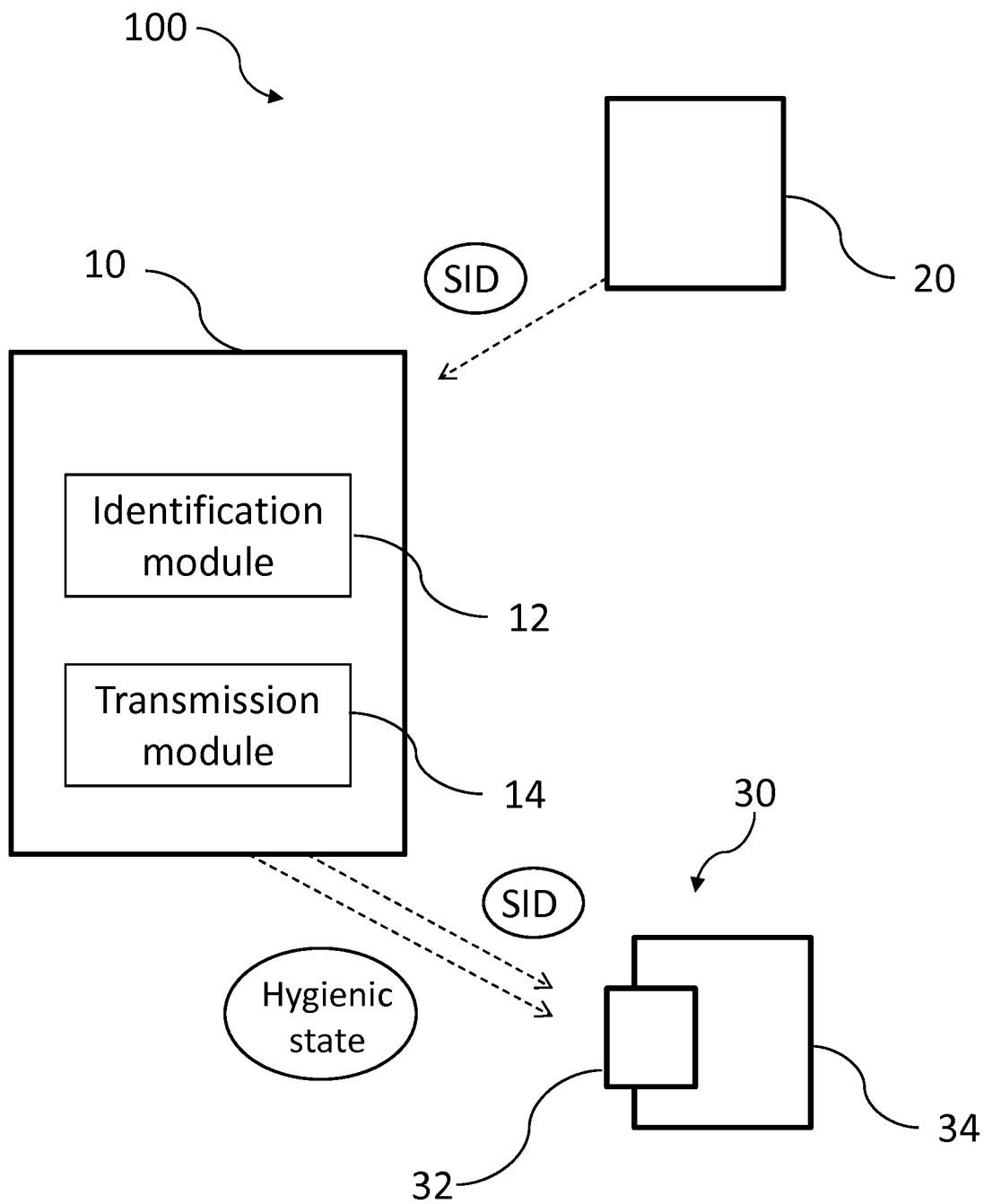
FIG. 1 shows a schematic view of a hygiene monitoring system comprising a hygiene monitoring device, a station device, and a receiving entity in accordance with an embodiment of the present disclosure.

FIG. 1 shows a hygiene monitoring system 100 for monitoring a hygienic state of a user.

The hygiene monitoring system 100 comprises a hygiene monitoring device 10, a station device 20 and a receiving entity 30.

The hygiene monitoring device 10 may be removably attached to a hygiene article of a user so that it may monitor the hygienic state of the hygiene article. A hygiene article may, for example, be a diaper, a sanitary pad, or similar article used to contain bodily fluids or exudates, to improve the comfort and sanitary condition of the wearer.

As will be explained below, the hygiene monitoring device 10 may comprise a sensor, such as an electrode strip 13, configured to sense a hygienic state of the hygiene article. The hygiene monitoring device may, based on information sensed by the sensor, detect a hygienic state of the user, for example a hygienic event such as a soiling event.

The station device 20 permanently or semi-permanently stores a station identifier SID corresponding to the station device 20. The station identifier SID is unique within the hygiene monitoring system 100.

The hygiene monitoring device 10 comprises an identification module 12 configured to obtain the station identifier SID from the station device, and to store the station identifier SID in memory of the hygiene monitoring device 10.

In the present embodiment, the identification module 12 comprises a receiver (not shown) which is configured to receive a station identifier SID transmitted by the station device 20 via wireless means, for example, infra-red communication (IR, such as IRdA), radio frequency identification (RFID) or near-field communication (NFC).

As can be seen on FIG. 1, in this embodiment, hygiene monitoring device 10 further comprises a transmission module 14, which is configured to transmit the stored station identifier SID and/or information indicative of a hygienic state of the hygiene article monitored by the hygiene monitoring device 10, to the receiving entity 30. In this embodiment, the transmission module 14 transmits information via wireless communication, such as WLAN/WiFi/WiMAX, communication in accordance with IEEE 802.11 a, b, g, n protocols, cellular communication such as GSM/GPRS communication or 3G/4G/LTE communication, long-range Bluetooth™ and the like.

In the present embodiment, the receiving entity 30 comprises a gateway 32 and a server 34 which are communicatively coupled to one another. The gateway 32 is configured to receive the information from the hygiene monitoring device 10 (e.g., the station identifier SID and/or the information indicative of the hygienic state) via wireless communication, and to forward the received information to the server 34, which is configured to notify of a hygienic state detected by the hygiene monitoring device 10 and a corresponding spatial location corresponding to the station device 20.

Figure 2:
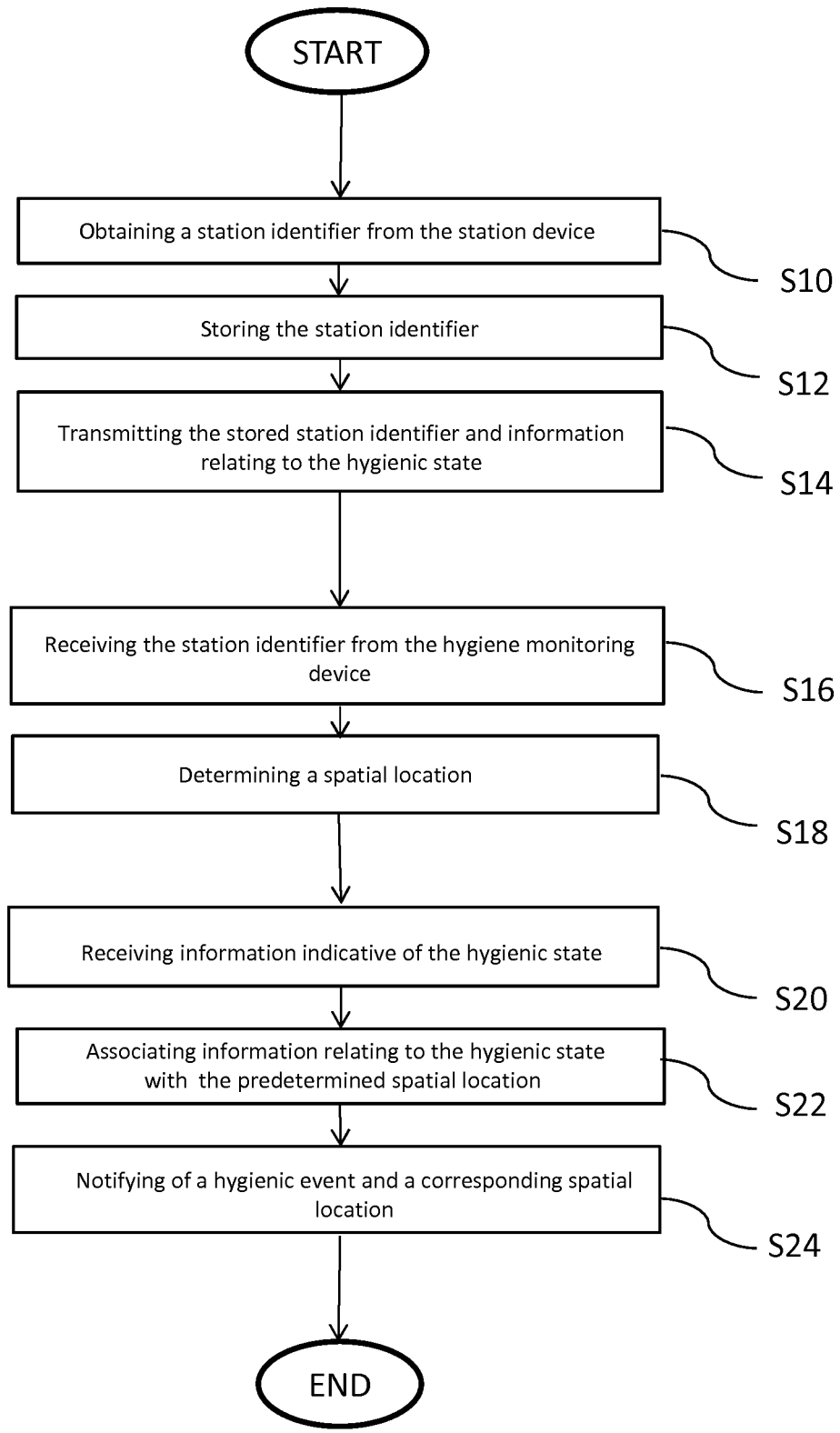
FIG. 2 shows a flowchart of a method in accordance with a modified embodiment of the present disclosure.

As explained below in relation to FIG. 2, there is described an implementation of associating a hygiene monitoring device 10 to a station device 20, so as to notify of a hygienic state detected by the hygiene monitoring device 10 and a spatial location corresponding to the station device 20.

In step S10, the hygiene monitoring device 10 obtains, when in use, the station identifier SID from the station device 20.

Then, in step S12, the hygiene monitoring device 10 stores the received station identifier SID, for example in a memory, such as a working memory or a non-volatile memory, of the hygiene monitoring device 10.

In step S14, the hygiene monitoring device 10 transmits the stored station identifier SID and information indicative of the hygienic state of the article to the receiving entity 30. The transmission of the station identifier and the information indicative of the hygienic state of the article may be simultaneous or contemporaneous, or the two may be transmitted separately, for example, at a predetermined interval from one another. The transmission may be triggered by a user interacting with a user interface element of the station or of the hygiene monitoring device, such as pressing a button or touching a touch element, or by the monitoring device detecting a change in the monitored state, such as a change indicative of a hygienic event.

In step S16, the receiving entity 30 receives the station identifier SID from the hygiene monitoring device 10.

Upon receiving the station identifier SID, the receiving entity 30 determines a spatial location corresponding to the station identifier SID in step S18. In the present embodiment, the spatial location corresponding to the station identifier SID is the spatial location of the station device 20 itself.

The server 32 determines the spatial location of the station device 20 by obtaining a relationship between the received station identifier SID and the spatial location of the station device 20, for example, by accessing a database storing one-to-one correspondences between multiple station identifiers and corresponding spatial locations of the respective station devices. Advantageously, the station device may be installed permanently by fixing it to a structural element of the care home, such as a wall, ceiling or floor. Otherwise, the station device may simply be placed at a suitable location, such as on a table or shelf.

In step S20, the receiving entity 30 receives the information indicative of the hygienic state of the article from the hygiene monitoring device 10. Although steps S16 and S20 are shown as two separate sequential steps, these may occur at the same time, or in the opposite order.

In step S22, the receiving device associates the information indicative of the hygienic state of the article received from the hygiene monitoring device 10, and the determined spatial location of the station device 20.

If a notification of a hygienic state is required, in step S24, the server 32 alerts a caregiver by any means, such as a visual, auditory and/or sensory notification means.

Such a notification provides the caregiver receiving it with the determined spatial location of the station device 20 associated with the received information indicative of the hygienic state of the article, and, optionally, with information indicating the hygienic state of the article. The caregiver may then readily understand which location requires attention (i.e., the determined spatial location corresponding to the station device 20), and, therefore, which resident requires attention.

Figure 3:
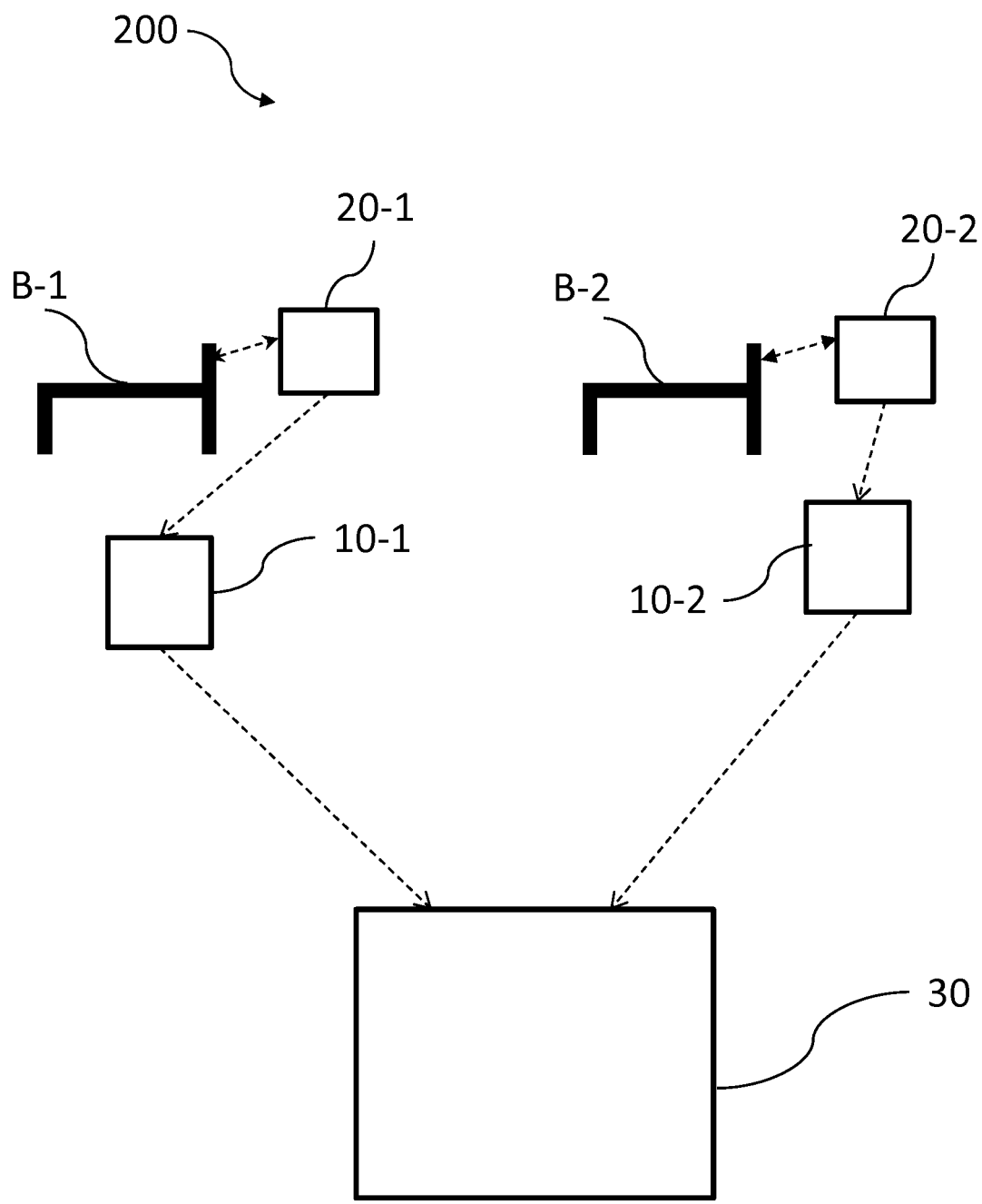
FIG. 3 shows a flowchart of a method in accordance with an embodiment of the present disclosure.

FIG. 3 shows a hygiene monitoring system 200 comprising two hygiene monitoring devices 10-1 and 10-2, two station devices 20-1 and 20-2, and a common receiving entity 30. Each of the hygiene monitoring devices 10-1, 10-2 are of the type described above. Each of the two station devices 20-1, 20-2 are of the type described above. Each of the station devices 20-1, 20-2 are permanently or semi-permanently associated with respective beds B-1 and B-2, for example, by fixation to the respective beds B-1, B-2.

The station devices 20-1, 20-2 each store a respective station identifier which is unique in the system 200, in the manner described above.

Each of the hygiene monitoring devices 10-1, 10-2 may be associated with either of the station devices 20-1, 20-2 by obtaining their corresponding station identifier in the manner described above.

Each of the hygiene monitoring devices 10-1, 10-2 may be removably attached to different hygiene articles of different users, so that they may each monitor the hygiene state of the respective hygiene articles.

As described herein, each of the hygiene monitoring devices 10-1, 10-2 are configured transmit the station identifier SID they respectively store and information indicative of the hygienic state of the article to the receiving entity 30, in a manner described above in connection with FIG. 2.

The receiving entity 30 is configured to receive the respective station identifier SID from each of the hygiene monitoring devices 10-1, 10-2.

Upon receiving information indicative of a hygienic state together with a station identifier from either hygiene monitoring device 10-1 or 10-2, the receiving entity 30 determines a spatial location (for example, bed B-1 or bed B-2) as described above in relation to FIG. 2. If it is determined that a notification is required, the receiving entity 30 may alert a caregiver in the manner described above.

Such a notification provides the caregiver receiving it with the determined spatial location of the relevant station device 20-1 or 20-2 (i.e., bed B-1 or bed B-2) associated with the received information indicative of the hygienic state of the relevant article, and, optionally, with information indicating the hygienic state of the relevant article. The caregiver may then readily understand which location (bed B-1 or bed B-2) requires attention (i.e., the determined spatial location corresponding to the station device 20), and, therefore, which resident requires attention.

Even though the above embodiment includes two hygiene monitoring devices and two station devices, the hygiene monitoring device may include any number of hygiene monitoring devices and station devices, and the number of hygiene monitoring devices and the number of station devices are independent from one another.

In the above described implementation of associating a hygiene monitoring device 10 to a station device 20, the hygiene monitoring device 10 transmits the stored station identifier SID and information indicative of the hygienic state of the article to the receiving entity 30.

Figure 4:
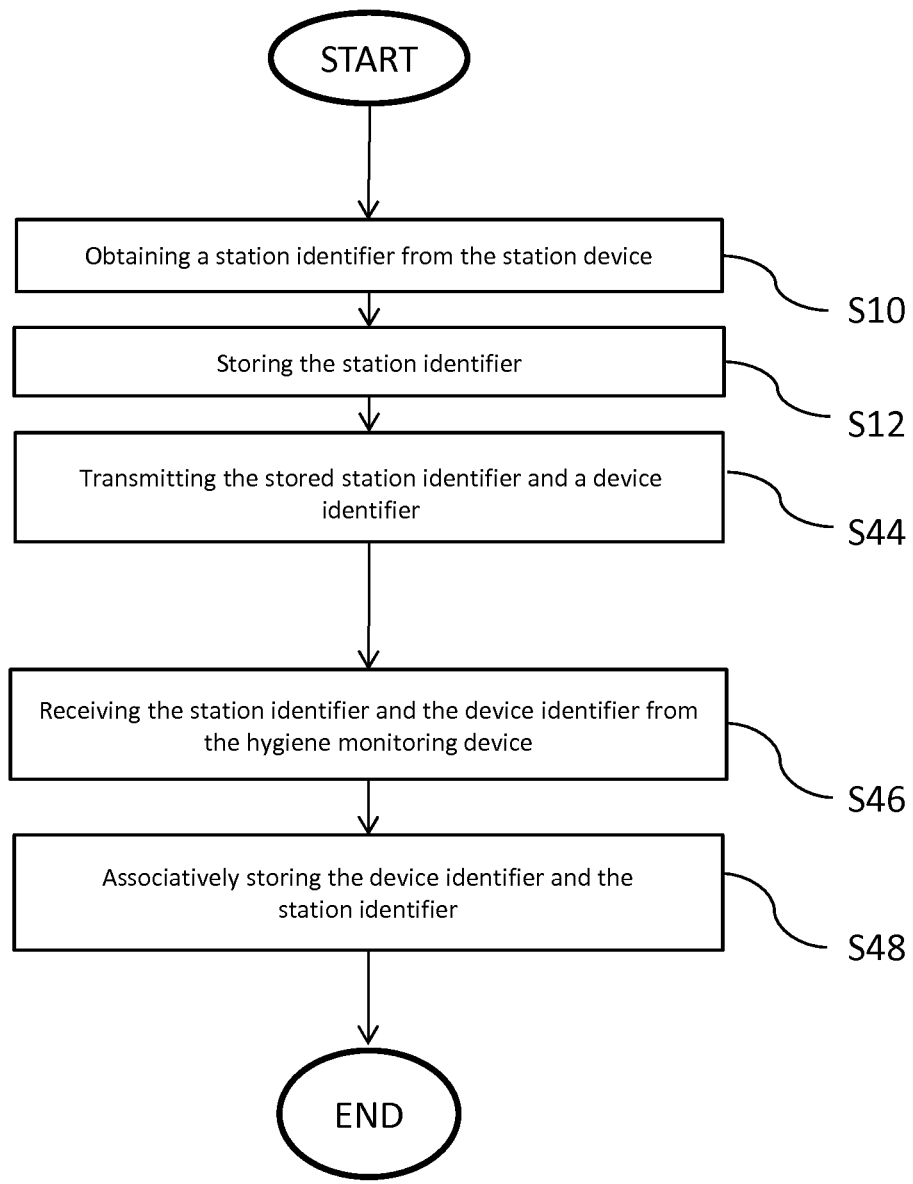
FIG. 4 shows a flowchart of a method in accordance with a modification of the embodiment of the present disclosure.

A modification of the above implementation will be described with reference to FIG. 4.

In the modification to the implementation, the hygiene monitoring device 10 obtains a station identifier SID corresponding to a station device 20 and stores the station identifier SID in the manner explained above with reference to FIGS. 1-3 and steps S10 and S12.

However, in the present modification, the hygiene monitoring device 10 stores (permanently or semi-permanently) a device identifier DID for identifying the hygiene monitoring device 10 in the system 100 or 200. More specifically, the device identifier DID may be a piece of information which corresponds to the hygiene monitoring device 10, thereby allowing the hygiene monitoring device 10 to be differentiated from other hygiene monitoring devices in the system. In other words, the device identifier DID uniquely identifies the hygiene monitoring device 10 in the hygiene monitoring system 100 or 200.

The device identifier DID is pre-stored in a memory, here a non-volatile memory, of the hygiene monitoring device 10 for subsequent access.

Following steps S10 and S12 as described above, in step S44, the hygiene monitoring device 10 transmits the stored station identifier SID and the device identifier DID to the receiving entity 30.

In step S46, the receiving entity 30 receives the stored station identifier SID and the device identifier DID from the hygiene monitoring device 10.

Upon receiving the station identifier SID and the device identifier DID from the hygiene monitoring device 10, the receiving entity 30 associatively stores in step S48 the device identifier DID and the station identifier SID. This in turn allows for a relationship between the device identifier DID and a spatial location corresponding to the station device 20 to be established, based on a pre-stored relationship between the received station identifier SID and the spatial location of the station device 20, as explained above with reference to step S22.

Consequently, the above implementation can be used to determine a spatial location corresponding to the hygiene monitoring device 10.

The receiving entity 30 causes the relationship between the device identifier DID and a spatial location to be stored in a database storing one-to-one correspondences between device identifiers DID and station identifiers SIDs, which, in turn each corresponds to a station device 20, or stored in a database storing one-to-one correspondences between device identifiers DID and station devices 20 directly.

Subsequently, the hygiene monitoring device 10 transmits the stored device identifier DID and information indicative of the hygienic state of the article to the receiving entity 30, without transmitting the station identifier SID. In fact, in certain embodiments, after having transmitted the device identifier DID and the stored station identifier SID to the receiving entity in step S44, the hygiene monitoring device may delete the stored station identifier SID.

The device identifier DID and the information indicative of the hygienic state of the article may be transmitted simultaneously or contemporaneously, or the two may be transmitted separately (for example, at a predetermined interval from one another), in a similar manner to that explained in relation to step S14 above with reference to the station identifier SID, instead of the device identifier DID.

The receiving entity 30 receives the DID device identifier and the information indicative of the hygienic state of the article monitored by the hygiene monitoring device 10, in a similar manner as explained above in relation to step S20 with reference to the station identifier SID instead of the device identifier DID.

The receiving entity 30 determines a spatial location corresponding to the station device 20, based on the association between the device identifier DID and the station identifier SID stored in step S48, in a similar manner to that explained in relation to step S18 above.

For example, the receiving entity 30 obtains the spatial location of the station device 20 by obtaining the stored correspondence between the received station identifier SID and the spatial location of the station device 20, for example, by accessing the database storing one-to-one correspondences between device identifiers DID and station identifiers SID, or the database storing one-to-one correspondences between device identifiers DID and station devices 20.

As explained above in relation to step S24, if a notification of a hygienic state is required, the receiving entity 30 alerts a caregiver by any means, such as a visual, auditory and/or sensory notification means.

In a similar manner to that explained above, such a notification provides the caregiver receiving it with the determined spatial location of the station device 20 associated with the received information indicative of the hygienic state of the article, and, optionally, with information indicating the hygienic state of the article. The caregiver may then readily understand which location requires attention (i.e., the determined spatial location corresponding to the station device 20), and, therefore, which resident requires attention.

Figure 5:
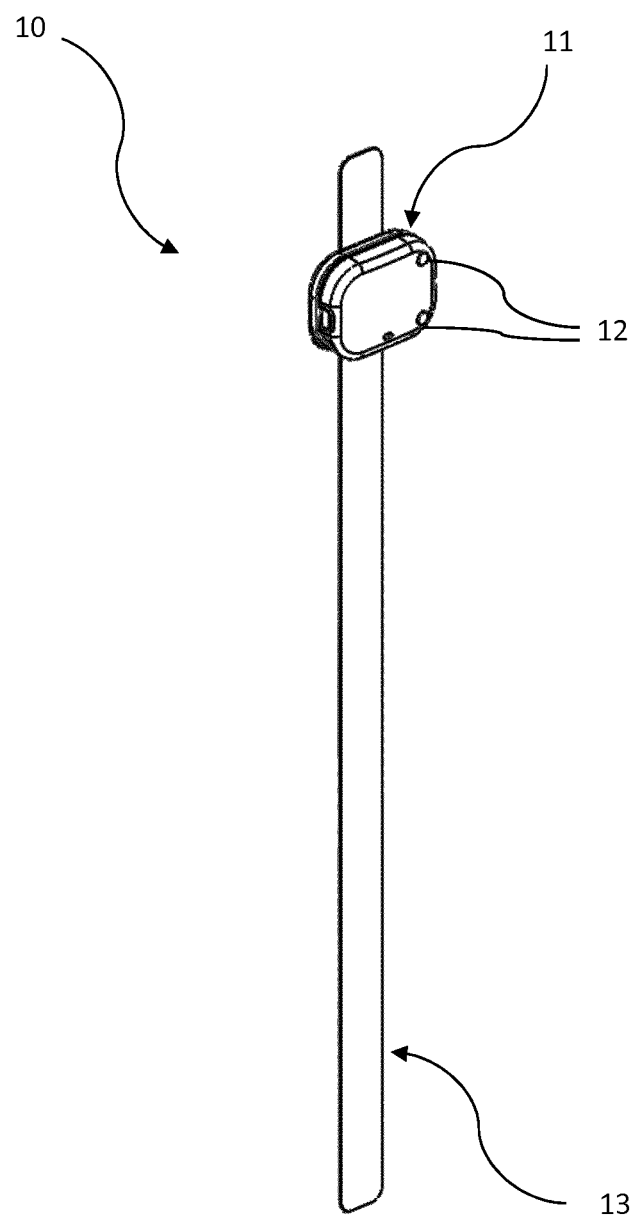
FIGS. 5 and 6 show a hygiene monitoring device for monitoring a hygienic state of a user.
Figure 6:
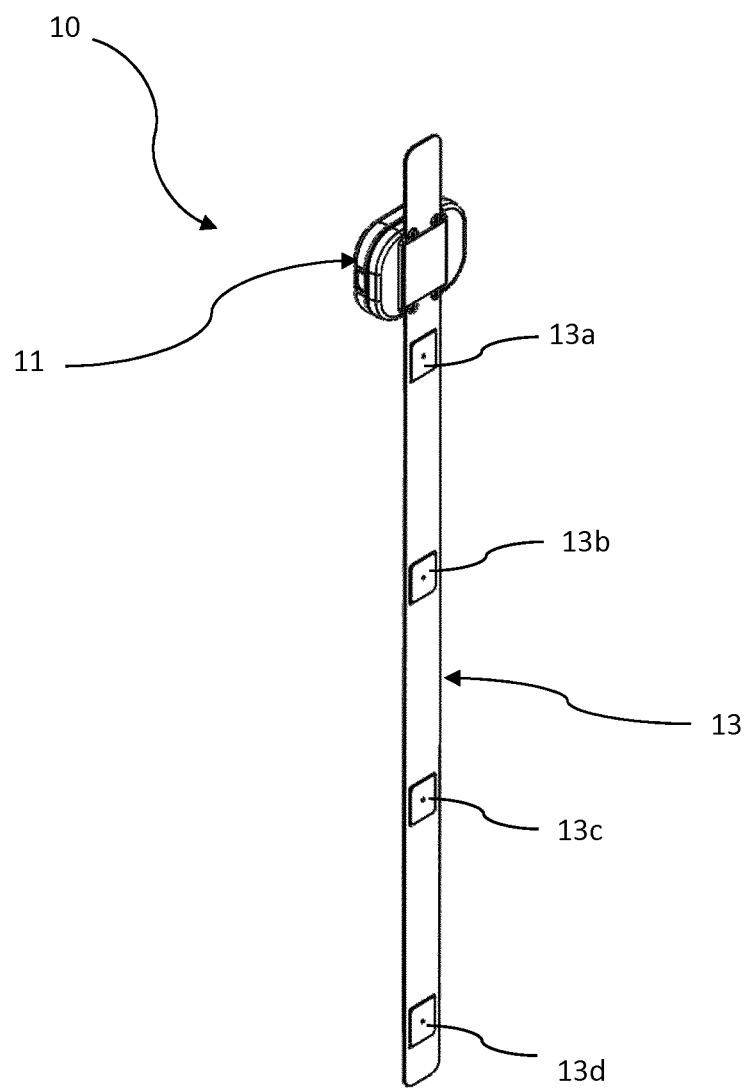

FIGS. 5 and 6 show an exemplary embodiment of a hygiene monitoring device 10 for use with any of the methods or systems described herein.

The hygiene monitoring device 10 is for monitoring a hygienic state of a user. The hygiene monitoring device 10 may be removably attached to a wearable article of a user so that it may monitor the hygienic state of the article.

The hygiene monitoring device 10 comprises a housing 11 and an electrode strip 13 which extends from the housing 11. As shown in FIGS. 5 and 6, the electrode strip 13 extends on both sides of the housing 11. In other embodiments, the electrode strip 13 may extend on only one side of the housing 11.

The housing 11 has an identification module 12 comprising two spaced-apart photodiodes. As noted above, the identification module 12 is for obtaining a station identifier SID from the station device 20.

As shown in FIG. 6, the electrode strip 13 of the hygiene monitoring device 10 comprises four electrodes 13a-13d which are spaced apart along the longitudinal length of the electrode strip 13. The hygiene monitoring device 10 is configured such that the electrodes 13a-13d may be brought into contact with the wearable article such that they may measure the hygienic state of the article, for example, by measurement of the wetness level of the article, presence of particular chemical compounds/compositions and/or pH levels. The specific arrangements of the electrodes will be known to a person skilled in the art, and, for example, may include any of the arrangements disclosed in WO 2016/090492, the contents of which are hereby incorporated by reference to the extent permitted by law.

Figure 7:
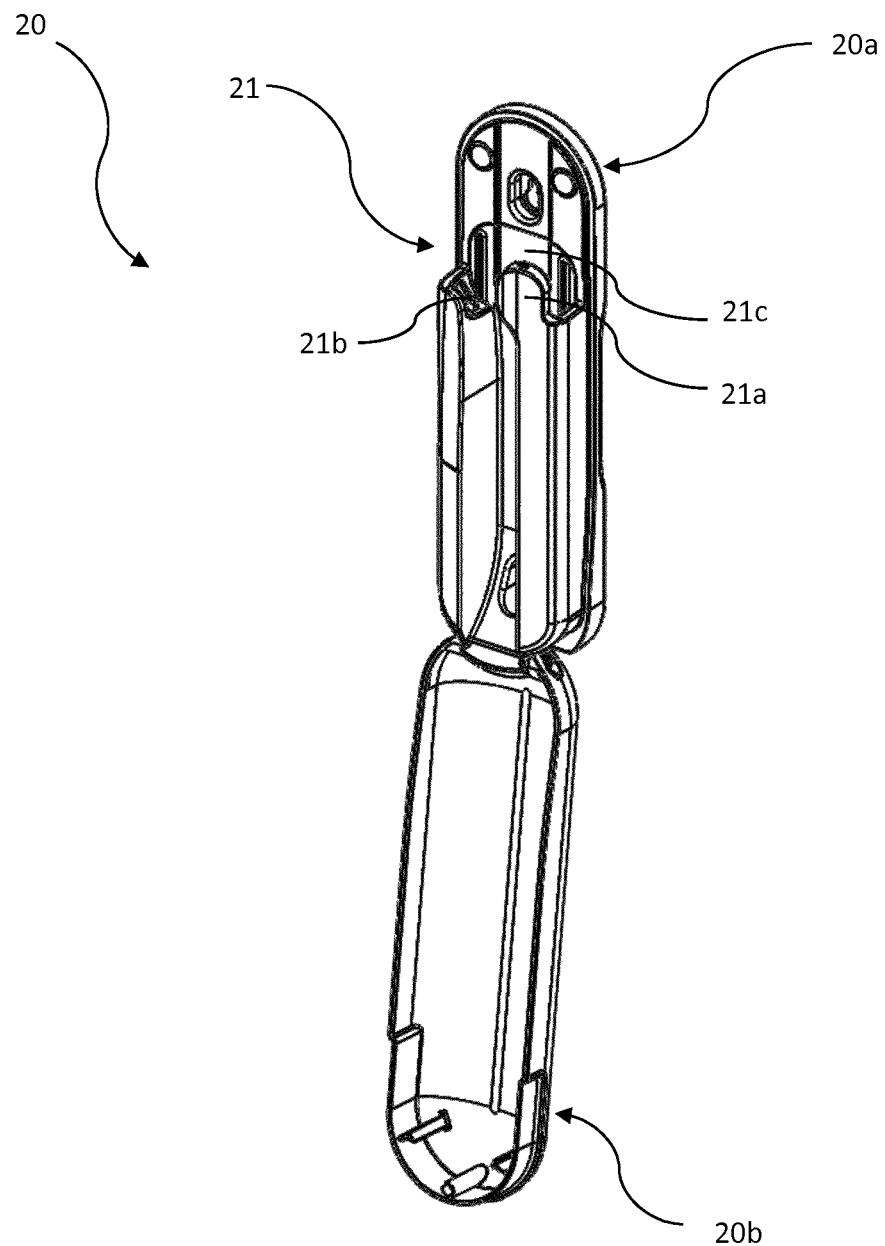
FIGS. 7 and 8 show a station device for receiving the hygiene monitoring device shown in FIGS. 5 and 6.

FIG. 7 shows an exemplary embodiment of a station device 20 for use with any of the methods or systems described herein.

The station device 20 is for receiving and storing the hygiene monitoring device 10. The station device 20 comprises a first casing portion 20a and a second casing portion 20b. The second casing portion 20b is pivotable relative to the first casing portion 20a so as to open and close the station 20. In certain embodiments, the station device 20 is configured to charge the hygiene monitoring device 10 when the hygiene monitoring device 10 is received in the station device 20.

The station device 20 comprises a securing component 21 which is configured to receive and hold the housing 11 of the hygiene monitoring device 10 at a defined location relative to the station device 20.

The securing component 21 comprises a first flange 21a, a second flange 21b, a back wall 21c, a first shelf (not shown) and a second shelf (not shown). The first shelf corresponds to the first flange 21a and the second shelf corresponds to the second flange 21b. The securing component 21 defines a cavity delimited by the first flange 21a, the second flange 21b, the back wall 21c, the first shelf and the second shelf.

The hygiene monitoring device 10 may be received in the station device 20 by inserting the housing 11 into the cavity defined by the securing component 21. Once the housing 11 is inserted, the securing component 21 holds the housing 11 in place such that the hygiene monitoring device 10 is held at a defined location relative to the station device 20.

The first flange 21a of the securing component 21 has a station identifier component (not shown) comprising two spaced-apart LEDs which act as transmitters. The station identifier component is configured to store a station identifier which is associated with the station device 20, as described above. The station identifier component is configured to transmit the station identifier using the LEDs to the identification module 12 when the housing 11 is received in the securing component 21.

Figure 8:
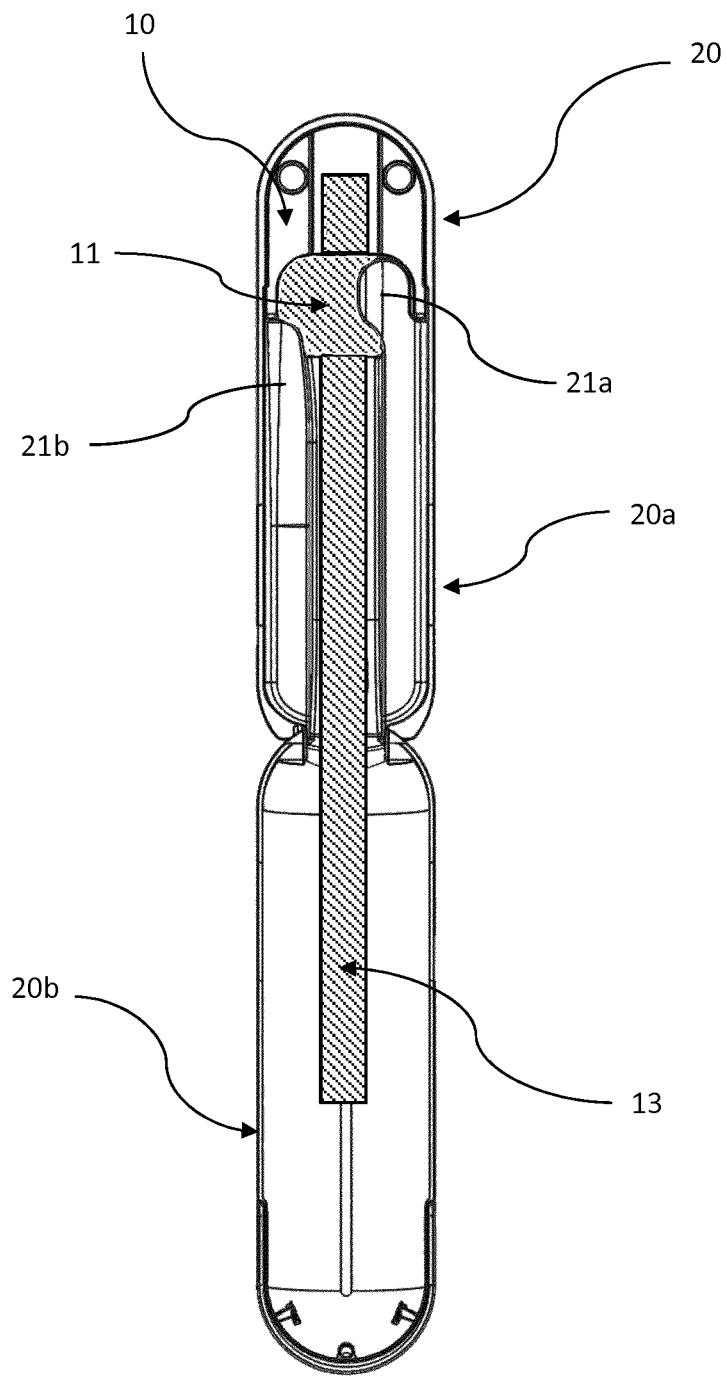

FIG. 8 shows the hygiene monitoring device 10 received in the station device 20. In this configuration, as noted above, the hygiene monitoring device 10 is able to, when in use, receive the station identifier SID from the station device 20.

Although the above explanation is considered to fully clarify how the present disclosure may straightforwardly be put into effect by those skilled in the art, it is to be regarded as purely exemplary.

For example, although in the above embodiment the hygiene monitoring device is configured to transmit information such the stored station identifier and/or the device identifier and the information indicative about the hygienic state, the hygiene monitoring device may alternatively merely store this information for retrieval by an external device (e.g., the station device) without any transmission from the hygiene monitoring device itself.

In certain cases, the hygiene monitoring device does not transmit any information indicative of the hygienic state, as no hygiene state necessitating a caregiver's attention is required.

Although in the above embodiment the receiving entity comprises a gateway 32, this is not necessary so long as the information can be received by the server 34, or the receiving entity 30 more generally.

Although the steps in sequential order, it will be clear to the person skilled in the art that not all of the steps shown in the Figures need to occur in the shown order, or not all steps are essential (e.g., the transmission of information indicative of the hygienic state and the related steps may not occur).

Although the above embodiments describe systems with a single receiving entity, it will be clear to the person skilled in the art that the present disclosure is not limited in the number of receiving entities, or in the number of hygiene monitoring device or station devices.

In fact, although the above described systems have a receiving entity separate from the station device, the station device may act as the receiver of transmissions from the hygiene monitoring device and therefore form part of the "receiving entity".

In the above embodiments, a caregiver may be alerted via visual, auditory and/or sensory notification means, for example, by transmitting a notification to a notification device (e.g., a portable user device) carried by the caregiver. For example, the caregivers may carry an iPod/iPad™ or any other kind of portable user device and receive alerts on their portable device indicating the location relevant to the alert. The notification device may be configured to receiving alerts corresponding to a predetermined set of spatial locations, beds, e.g., in a situation where a plurality of caregivers at a nursing home are each assigned care for a separate set of specific residents.

The embodiments above have been defined functionally, since the skilled reader will understand how such functionality may be provided using commodity or bespoke electronic data processing equipment. However, for the avoidance of doubt, each functional unit may be implemented as a standard microprocessor, equipped with working memory, instruction store, data store, communications bus, and appropriate interfaces to provide the functionality described. The functional units can also be provided as discrete logic, as Application Specific Integrated Circuits (ASICs), without limitation.

Even though the above has been described in relation to use in a care home, the above system is suitable for use in any institution/location, such as a hospital or nursery.

Although the above has been described generally in relation to permanently fixed station devices, it will be apparent that the station devices need not remain permanently at the same location. The above described may, for example, provide the possibility of replacing a station device or associating a station device with a new spatial location.

All of the above is fully in the scope of the disclosure and are considered to form the basis for alternative embodiments in which one or more combinations of the above-described features are applied, without limitation to the specific combinations disclosed above.

In light of this, there will be many alternatives which implement the teaching of the present disclosure. It is expected that one skilled in the art will be able to modify and adapt the above disclosure to suit their own circumstances and requirements within the scope of the present disclosure, while retaining some or all technical effects of the same, either disclosed or derivable from the above, in light of his common general knowledge in this art. All such equivalent modifications or adaptations fall within the scope of the present invention as defined by the appended claims.

What is claimed is:

1. A method of associating a hygiene monitoring device to a station device, the hygiene monitoring device being configured to monitor a hygienic state of a user, the method comprising:
    coupling the hygiene monitoring device to a user located at a defined spatial region which is in proximity of the station device, the hygiene monitoring device configured to monitor a hygienic state of the user and configured to transmit hygienic information indicative of the hygienic state of the user;
    the hygiene monitoring device obtaining, when in use, a station identifier (SID) from the station device located at the defined spatial region along with the user;
    the hygiene monitoring device at least one of storing the station identifier and transmitting the stored station identifier along with the hygienic information;
    receiving, by a receiving entity, the station identifier and the hygienic information from the hygiene monitoring device;
    determining, by the receiving entity, a spatial location corresponding to the station device based on the received station identifier, and the hygienic state of the user based on the hygienic information;
    in response to detecting a change in the hygienic state of the user based on the received hygienic information, transmitting a notification information from the receiving entity, the notification information including an alert of the change in the hygienic state of the user and the station identifier indicative of the spatial region at which the station device and the hygiene monitoring device coupled to the user are both located,
    wherein the hygiene monitoring device obtains the station identifier when placed within the defined spatial region in the proximity of the station device so as to provide an association between the hygiene monitoring device and the user with which the defined spatial region is associated, and
    wherein the hygiene monitoring device is removably attachable to a disposable absorbent hygiene article wearable by the user, and monitors a hygienic state of the disposable absorbent hygiene article, the hygienic state including a soiling event.

2. The method of claim 1, wherein the hygiene monitoring device stores a device identifier (DID), the method comprising:
    the hygiene monitoring device transmitting the stored station identifier together with the device identifier.

3. The method of claim 1, comprising:
    the station device verifying whether the station identifier is correctly obtained and/or stored by the hygiene monitoring device.

4. The method of claim 1, wherein the station device transmits the station identifier wirelessly.

5. The method of claim 1, wherein the station device continuously provides the station identifier or provides the station identifier selectively, based on a predetermined condition,
    and, optionally, the station device broadcasts the station identifier to provide it.

6. The method of claim 2, comprising:
    the receiving entity associatively storing the device identifier and the station identifier, and.

7. The method of claim 1, wherein the spatial location is determined based on a pre-stored correspondence between the station identifier and the spatial location.

8. The method according to claim 1, comprising:
    the receiving entity triggering a notification to one or more notification devices, the notification comprising at least information on the determined spatial location.

9. A hygiene monitoring device configured to monitor a hygienic state of a user, the hygiene monitoring device comprising:
    an identification module configured to obtain, when in use, a station identifier from a station device located at the defined spatial region along with the user, and to store the station identifier;
    a transmission module configured to transmit the station identifier and hygienic information indicative of the hygienic state of the user to a receiving entity remotely located from the station device and the hygiene monitoring device such that the receiving entity obtains a station identifier and hygienic information indicating the hygienic state of the user, determines the spatial region of the station device corresponding to the station identifier, and determines the hygienic state of the user based on the hygienic information, and in response to detecting a change in the hygienic state of the hygiene article based on the received hygienic information the receiving entity transmits a notification including an alert of the change in the hygienic state of the user and the station identifier indicative of the spatial region at which the station device and the hygiene monitoring device coupled to the user are both located;
    wherein an area surrounding the station device defines the spatial region in which the station device wirelessly exchanges information with the identification module,
    wherein the hygiene monitoring device is configured to be coupled to the user located at the defined spatial region which is in proximity of the station device;
    wherein the identification module is configured to obtain the station identifier when the hygiene monitoring device is placed within a defined spatial region in the proximity of the station device so as to provide an association between the hygiene monitoring device and a user with which the defined spatial region is associated, and
    wherein coupling the hygiene monitoring device to the user located at the defined spatial region which is in proximity of the station device includes the hygiene monitoring device being removably attachable to a disposable absorbent hygiene article and the hygiene monitoring device is configured to monitor a hygienic state of the disposable absorbent hygiene article, the hygienic state including a soiling event.

10. The hygiene monitoring device of claim 9, comprising:
a transmission module configured to transmit the stored station identifier.

11. The hygiene monitoring device of claim 9, wherein:
the identification module is configured to store a device identifier, and
the transmission module configured to transmit the stored station identifier together with the device identifier.

12. The hygiene monitoring device of claim 9, wherein the hygiene monitoring device is configured to transmit information indicating a hygienic state.

13. A hygiene monitoring system comprising:
the hygiene monitoring device of claim 9, the hygiene monitoring device configured to monitor a hygienic state of a hygiene article coupled to a user and configured to transmit hygienic information indicative of the hygienic state of the hygiene article;
a station device configured to provide the station identifier to the hygiene monitoring device when the hygiene monitoring device is placed within a defined spatial region in the proximity of the station device; and
a receiving entity remotely located from the station device and the hygiene monitoring device, the receiving entity configured to obtain a station identifier, and at least one of a device identifier and hygienic information indicating the hygienic state of the hygiene article, configured to determine the spatial region of the station device corresponding to the station identifier, and configured to determine the hygienic state of the hygiene article based on the hygienic information,
wherein in response to detecting a change in the hygienic state of the hygiene article based on the received hygienic information, the receiving entity transmits a notification including an alert of the change in the hygienic state of the hygiene article and the station identifier indicative of the spatial region at which the station device and the hygiene monitoring device coupled to the user are both located.

14. The hygiene monitoring system of claim 13, wherein:
the station device is configured to store the hygiene monitoring device and/or to charge the hygiene monitoring device; and wherein the station device is configured to provide the station identifier to the hygiene monitoring device when the hygiene monitoring device is stored and/or being charged by the station device.

15. The hygiene monitoring system of claim 13, comprising at least one notification device each adapted to display a notification corresponding to a hygienic event and a corresponding spatial location,
wherein the receiving entity is configured to trigger the notification on one or more of the at least one notification device.

16. The method of claim 1, comprising:
the hygiene monitoring device transmitting information indicative of a hygienic state together with the stored station identifier.

17. The method of claim 2, comprising:
the hygiene monitoring device transmitting information indicative of the hygienic state together with the device identifier.

18. The method of claim 4, wherein the station device transmits the station identifier via infra-red communication (IR), near-field communication (NFC), radio frequency identification (RFID), Bluetooth communication, WiFi communication, ultra-wide band communication, or via an sonic signal.

19. The method of claim 1, comprising:
the receiving entity notifying of a hygienic event and a corresponding spatial location of the hygienic event.

20. The method of claim 8, comprising:
the one or more notification devices displaying a notification when the notification corresponds to one of a predetermined set of spatial locations.

21. The hygiene monitoring system of claim 13, wherein:
the receiving entity is configured to notify of a hygienic event and a corresponding spatial location of the hygienic event.

22. The hygiene monitoring system of claim 15, wherein:
the at least one notification device are each configured to display notifications corresponding to a predetermined set of spatial locations.

* * * * *